United States Patent
Park et al.

(10) Patent No.: US 10,066,255 B2
(45) Date of Patent: Sep. 4, 2018

(54) PRETREATMENT METHOD FOR BACTERIAL IDENTIFICATION AND ANTIMICROBIAL SUSCEPTIBILITY TESTING OF POSITIVE BLOOD CULTURE SAMPLES

(71) Applicant: THE CATHOLIC UNIVERSITY OF KOREA INDUSTRY-ACADEMIC COOPERATION FOUNDATION, Seoul (KR)

(72) Inventors: Yeon Joon Park, Seoul (KR); Kang Gyun Park, Yongin-si (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 236 days.

(21) Appl. No.: 15/235,950

(22) Filed: Aug. 12, 2016

(65) Prior Publication Data
US 2017/0218429 A1   Aug. 3, 2017

(30) Foreign Application Priority Data
Feb. 3, 2016   (KR) .................. 10-2016-0013370

(51) Int. Cl.
*C12Q 1/24* (2006.01)
*C12Q 1/04* (2006.01)
*C12Q 1/18* (2006.01)

(52) U.S. Cl.
CPC ................. *C12Q 1/24* (2013.01); *C12Q 1/04* (2013.01); *C12Q 1/18* (2013.01)

(58) Field of Classification Search
None
See application file for complete search history.

(56) References Cited

U.S. PATENT DOCUMENTS 9,790,534 B2 * 10/2017 Walsh ..................... C12Q 1/04

FOREIGN PATENT DOCUMENTS

JP          2015-508667 A      3/2015

\* cited by examiner

*Primary Examiner* — Brian Gangle
(74) *Attorney, Agent, or Firm* — Novick, Kim & Lee, PLLC; Sang Ho Lee

(57) ABSTRACT

Provided is a blood culture treatment technology, including a novel treatment technology of performing pretreatment of a positive blood culture to effectively remove foreign substances such as cells, etc., thereby omitting a subculturing process on a solid medium and realizing rapid selection of antimicrobial agents for patients. The pretreatment method of a positive blood culture sample for bacterial identification and antimicrobial susceptibility testing includes preparing a first liquid culture by centrifuging a portion of a liquid medium including the positive blood culture sample, washing a precipitate thus centrifuged with a solution including sodium chloride, and then suspending the precipitate in the solution including sodium chloride, and preparing a second liquid culture by passing the first liquid culture thus prepared through a pretreatment filter including a mesh structure.

6 Claims, 5 Drawing Sheets

Table 1. Comparison of identification and antimicrobial susceptibility testing results testing results between the direct method and the standard method

| Microorganism | N of isolates | N of correct identifications | Antimicrobial susceptibility test | | | | |
|---|---|---|---|---|---|---|---|
| | | | N of antimicrobials tested | Agreement | Minor error | Major error | Very Major error |
| Gram-positive | 146 | 108(73.9%) | 1,081 | 1,051(97.2%) | 24(2.2%) | 1(0.1%) | 5(0.5%) |
| Staphylococcus aureus | 36 | 34 | 357 | 354 | 1 | 0 | 2 |
| Staphylococcus epidermidis | 23 | 18 | 289 | 272 | 15 | 0 | 2 |
| Staphylococcus haemolyticus | 12 | 9 | 34 | 32 | 2 | 0 | 0 |
| Staphylococcus capitis | 8 | 5 | 136 | 133 | 2 | 0 | 1 |
| Staphylococcus hominis | 4 | 4 | 34 | 33 | 1 | 0 | 0 |
| Staphylococcus saprophyticus | 1 | 1 | 17 | 17 | 0 | 0 | 0 |
| Staphylococcus cohnii spp. urealyticus | 1 | 1 | | | | | |
| Enterococcus faecium | 23 | 21 | 144 | 143 | 1 | 0 | 0 |
| Enterococcus faecalis | 6 | 5 | 60 | 57 | 2 | 1 | 0 |
| Streptococcus mitis/oralis | 8 | 3 | | | | | |
| Streptococcus parasanguinis | 2 | 0 | | | | | |
| Streptococcus viridans group | 2 | 0 | | | | | |
| Streptococcus pneumoniae | 2 | 1 | 10 | 10 | 0 | 0 | 0 |
| Streptococcus gallolyticus ssp. pasteurianus | 1 | 0 | | | | | |
| Streptococcus constellatus ssp. constellatus | 1 | 0 | | | | | |
| Streptococcus salivarius | 1 | 0 | | | | | |
| Streptococcus mutans | 1 | 0 | | | | | |
| Streptococcus anginosus | 1 | 1 | | | | | |
| Micrococcus ssp. | 3 | 1 | | | | | |
| Aerococcus urinae | 1 | 1 | | | | | |
| Propionibacterium acnes | 4 | 3 | | | | | |
| Bacillus spp. | 2 | 0 | | | | | |

FIG. 4

| Organism | | | | | |
|---|---|---|---|---|---|
| Actinomyces odontolyticus | 1 | 0 | | | |
| Finegoldia magna | 1 | 0 | | | |
| Peptostreptococcus spp. | 1 | 0 | | | |
| Gram-negative | 108 | 100(92.6%) | 897 | 885(98.6%) | 12(1.4%) | 0 |
| Escherichia coli | 53 | 53 | 522 | 518 | 4 | 0 |
| Klebsiella pneumoniae | 14 | 13 | 162 | 160 | 2 | 0 |
| Salmonella spp. | 3 | 3 | | | | |
| Enterobacter cloacae | 4 | 4 | 18 | 18 | 0 | 0 |
| Enterobacter aerogenes | 3 | 3 | 36 | 36 | 0 | 0 |
| Klebsiella oxytoca | 3 | 3 | 36 | 36 | 0 | 0 |
| Serratia marcescens | 1 | 1 | 18 | 17 | 1 | 0 |
| Pantoea spp. | 1 | 0 | | | | |
| Providencia stuartii | 1 | 1 | 17 | 15 | 2 | 0 |
| Pseudomonas aeruginosa | 10 | 10 | 56 | 53 | 3 | 0 |
| Acinetobacter baumannii | 2 | 0 | 32 | 32 | 0 | 0 |
| Stenotrophomonas maltophilia | 2 | 2 | | | | |
| Burkholderia cepacia | 1 | 0 | | | | |
| Ralstonia mannitolilytica | 3 | 1 | | | | |
| Chryseobacterium indologenes(CDC IIb) | 1 | 0 | | | | |
| Haemophilus influenzae | 1 | 1 | | | | |
| Bacteroides fragilis | 2 | 2 | | | | |
| Clostridium tertium | 2 | 2 | | | | |
| Neisseria spp. | 1 | 1 | | | | |
| Total | 254 | 208(81.8%) | 1,978 | 1,936(97.9%) | 36(1.8%) | 5(0.25%) |

FIG. 5

PRETREATMENT METHOD FOR BACTERIAL IDENTIFICATION AND ANTIMICROBIAL SUSCEPTIBILITY TESTING OF POSITIVE BLOOD CULTURE SAMPLES

CROSS-REFERENCE TO RELATED APPLICATION

This application claims the benefit of Korean Patent Application No. 10-2016-0013370, filed on Feb. 3, 2016, in the Korean Intellectual Property Office, the disclosure of which is incorporated herein in its entirety by reference.

BACKGROUND

1. Field

The present disclosure relates to a technology of treating a positive blood culture sample used for bacterial identification and antimicrobial susceptibility testing which are performed for the treatment of bacteremia, etc. Specifically, the present disclosure relates to a technology of performing a pretreatment process when a positive signal is detected in a blood culture, thereby omitting the previous subculturing process and thus enabling a rapid examination.

2. Description of the Related Art

Bacteremia is a very serious type of infections, and treatment of bacteremia requires identification of causative bacteria and selection of appropriate antimicrobial agents to be used for the treatment of the corresponding bacteria. Due to a recent increase of multidrug resistant bacteria which are resistant to many drugs, infections caused by resistant bacteria have been pointed out as a global risk factor.

For selection of appropriate antimicrobial agents against these resistant bacteria, bacterial identification and antimicrobial susceptibility testing are essential. For these tests, subculturing of a liquid medium of a positive-signal blood culture on a solid medium is performed for 16 hrs to 18 hrs, and then grown colonies are used for testing.

However, since preparation of the culture for these known tests requires a very long time, there is a disadvantage that rapid selection of antimicrobial agents is very difficult.

To omit this subculturing process, Japanese Patent Publication No. 2015-508667 suggests a technology of using a chemical buffering agent for isolation of bacteria from a positive blood culture. However, when chemicals are used to isolate microorganisms, there is a problem that it is very difficult to completely remove cells, etc., which may affect bacterial identification and antimicrobial susceptibility testing.

SUMMARY

An object of the present disclosure is to provide a blood culture treatment technology, including a novel treatment technology of lysing blood cells using a simple compound and then performing pretreatment of a positive blood culture by a physical method of using a filter to effectively remove foreign substances such as cells, etc., thereby omitting a subculturing process on a solid medium, enabling accurate bacterial identification and antimicrobial susceptibility testing, and realizing rapid, accurate selection of antimicrobial agents for patients.

To achieve the above object, there is provided a pretreatment method of a positive blood culture sample for bacterial identification and antimicrobial susceptibility testing, which includes preparing a first liquid culture by centrifuging a portion of a liquid medium comprising the positive blood culture sample, washing a precipitate thus centrifuged with a solution including sodium chloride, and suspending the precipitate in the solution including sodium chloride, and preparing a second liquid culture by passing the first liquid culture thus prepared through a pretreatment filter comprising a mesh structure.

The pretreatment method may further include adding a solution comprising ammonium chloride and saponin to the precipitate to lyse blood cells, prior to the washing of the centrifuged precipitate.

BRIEF DESCRIPTION OF THE DRAWINGS

These and/or other aspects will become apparent and more readily appreciated from the following description of the embodiments, taken in conjunction with the accompanying drawings in which:

FIGS. 4 and 5 are a data analysis tables obtained by experiments regarding the pretreatment method according to an embodiment of the present inventive concept.

DETAILED DESCRIPTION

Figure 1:
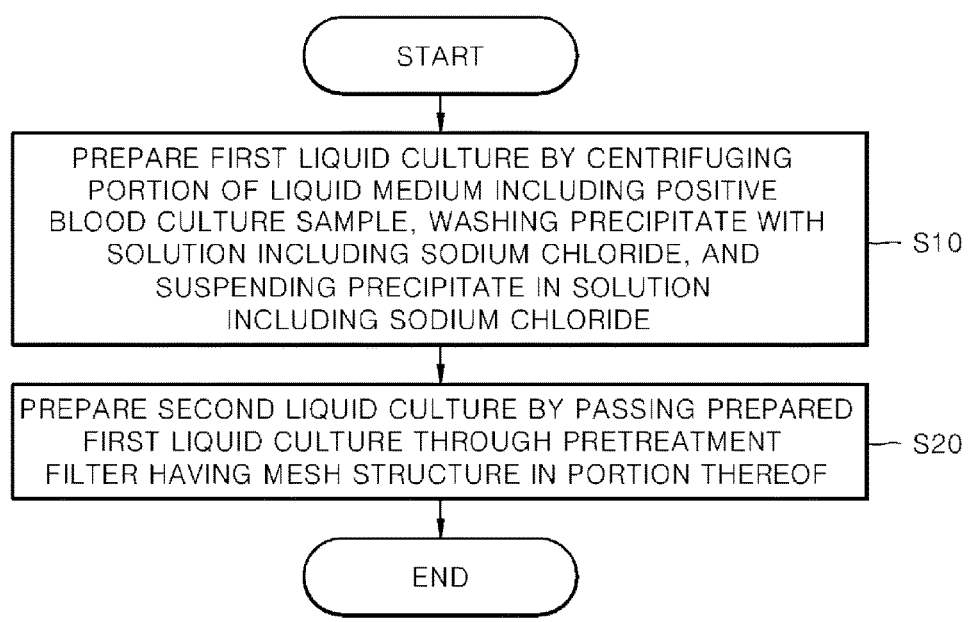
FIG. 1 is a flow chart of a pretreatment method of a positive blood culture sample for bacterial identification and antimicrobial susceptibility testing according to an embodiment of the present inventive concept.

In order to achieve the above object, a pretreatment method of a positive blood culture sample for bacterial identification and antimicrobial susceptibility testing according to an embodiment of the present inventive concept includes centrifuging a portion of a liquid medium including the positive blood culture sample, washing a precipitate thus centrifuged with a solution including sodium chloride, and then suspending the precipitate in the solution including sodium chloride to prepare a first liquid culture; and passing the first liquid culture thus prepared through a pretreatment filter including a mesh structure to prepare a second liquid culture.

The pretreatment method of the present inventive concept further includes adding a solution including ammonium chloride and saponin to the precipitate to lyse blood cells, prior to the washing of the centrifuged precipitate.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

Hereinafter, a pretreatment method of a positive blood culture sample for bacterial identification and antimicrobial susceptibility testing according to an embodiment of the present inventive concept will be described with reference to the accompanying drawings.

In the following description, in order to clearly understand the present inventive concept, description of a known technology regarding a characteristic of the present inventive concept will be omitted. It is obvious that the following exemplary embodiment is a detailed description which is provided for more understanding of the present inventive concept but does not limit the scope of the present inventive concept. Therefore, an equivalent inventive concept which performs the same function as the present inventive concept may be also covered by the scope of the present inventive concept.

In the following description, like reference numerals designate the same configuration, and redundant description and description of a known technology will be omitted.

FIG. 1 is a flow chart of a pretreatment method of a positive blood culture sample for bacterial identification and antimicrobial susceptibility testing according to an embodiment of the present inventive concept.

Referring to FIG. 1, the pretreatment method of the positive blood culture sample for bacterial identification and antimicrobial susceptibility testing according to an embodiment of the present inventive concept includes centrifuging a portion of a liquid medium including the positive blood culture sample, washing a precipitate thus centrifuged with a solution including sodium chloride, and then suspending the precipitate in the solution including sodium chloride to prepare a first liquid culture (S10), and passing the first liquid culture thus prepared through a pretreatment filter including a mesh structure to prepare a second liquid culture (S20).

Specifically, FIG. 1 shows a treatment process which is performed when a liquid medium including a positive signal-detected blood culture is an anaerobic culture bottle, and in the case of an aerobic culture bottle, the after-mentioned additional procedures may be performed.

A specific description of an experimental example regarding the anaerobic culture bottle is as follows. In S10, 10 ml of the liquid medium was taken, and then centrifuged at 4500 g for about 3 minutes. After centrifugation, the precipitate is produced, and this precipitate is washed with a 0.45% sodium chloride (NaCl) solution at predetermined times (e.g., twice).

Thereafter, the precipitate is suspended in about 10 ml of 0.45% sodium chloride solution to prepare the first liquid culture.

Meanwhile, with regard to the aerobic culture bottle, additional procedures are performed in S10. When the precipitate is produced by the centrifugation, a lysis solution of about 0.1 ml of a 9.26% ammonium chloride solution and about 5 ml of 2% saponin is added to the precipitate, followed by vortexing for 10 seconds. Then, the precipitate was left at room temperature for a predetermined time (e.g., 10 minutes).

Thereafter, the precipitate is washed with and suspended in the above mentioned sodium chloride solution to prepare the first liquid culture.

When the first liquid culture is prepared by performing S10, subculturing of the corresponding liquid culture on a solid medium is performed for about 16 hours to about 18 hours in the previous method. In the present inventive concept, however, the second liquid culture is prepared as in S20, and then used for bacterial identification and antimicrobial susceptibility testing.

Figure 2:
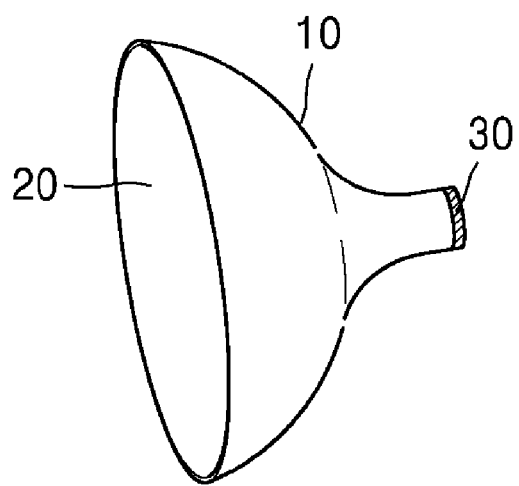
FIGS. 2 and 3 are schematic structural views of a pretreatment filter according to an embodiment of the present inventive concept.
Figure 3:
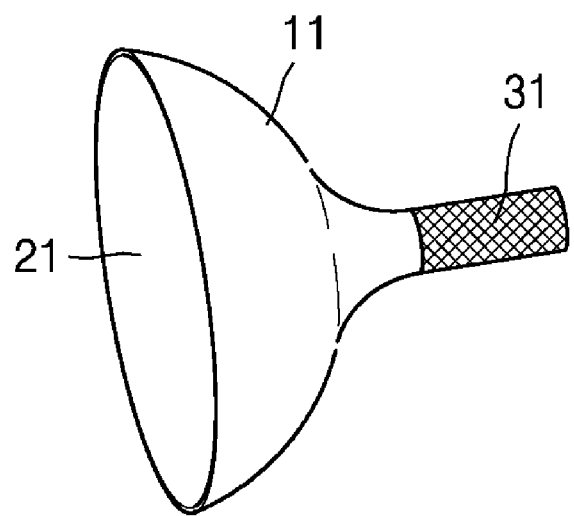

Specific examples of the pretreatment filter, through which the first liquid culture is filtered in S20, are illustrated in FIGS. 2 and 3. FIGS. 2 and 3 are schematic structural views of the pretreatment filter according to an embodiment of the present inventive concept.

Referring to FIG. 2, the pretreatment filter includes a body 10, a first end 20, and a second end 30. The first end 20 means an open end, into which the first liquid medium is introduced, and the second end 30 means an end, from which the second liquid medium obtained by filtering the first liquid medium is discharged, and the second end includes a surface composed of a mesh structure. That is, the second end surface is closed with a net of the mesh structure, thereby filtering cells. The body may have a conical configuration (funnel shaped), in which the second end 30 has a narrower diameter than the first end 20.

The mesh structure may be made of, for example, nylon and prepared to have a pore size of about 50 to 60 micrometers. This pore size may allow effective filtration of foreign substances such as cells, etc.

Meanwhile, referring to FIG. 3, in another embodiment of the present inventive concept, a body 11 and a first end 21 may be the same as in FIG. 2, but a second end 31 may be different from that in FIG. 2. That is, in the embodiment of FIG. 3, in addition to the second end surface, a portion of the second end side in the body 11 may be also composed of the mesh structure.

Returning to FIG. 1, the liquid culture prepared by S20 may be used in bacterial identification and antimicrobial susceptibility testing through the following post-treatment process.

That is, the post-treatment process in the present inventive concept means, for example, a process of centrifuging the second liquid culture (at 4500 g for about 3 minutes) and then suspending a precipitate thus centrifuged in a 0.45% sodium chloride solution.

Thereafter, the antimicrobial susceptibility testing is performed after turbidity of the suspension is adjusted to McF 0.5. In order to perform the bacterial identification by using a device, for example, Vitek MS MALDI-TOF, etc., the bacteria culture suspended in the sodium chloride solution is centrifuged, for example, at 15000 g for about 3 minutes, and then the precipitate is mixed with 20 ul of alcohol to be applied to a target plate.

When the testing is performed through these procedures, a culturing time of about 16 hours to 18 hours, which is spent on general subculturing (the previous method) of the liquid medium on the solid medium to avoid effects of cells, may be shortened, thereby performing rapid selection of appropriate antimicrobial agents for the treatment of bacteremia. As a result, prognosis of patients may be greatly affected.

An empirical experimental example of this effect is well illustrated in FIGS. 4 and 5.

FIGS. 4 and 5 are a data analysis tables obtained by experiments regarding the pretreatment method according to an embodiment of the present inventive concept.

Referring to FIGS. 4 and 5, when the pretreatment method according to an embodiment of the present inventive concept is compared with the previous method, they showed consistent bacterial identification results in 208 test samples (81.8%) out of total 254 blood culture bottles. These test samples were compared with each other with regard to Gram-positive bacteria and Gram-negative bacteria grown in the samples. Consistent bacterial identifications were observed in 108 (73.9%) out of 146 samples in which Gram-positive bacteria grew, and in 100 (92.6%) out of 108 samples in which Gram-negative bacteria grew.

The total number of bacterium/antimicrobial agent combinations used in the antimicrobial susceptibility testing was 1,978, and of them, consistency was observed in 97.2% of 1,081 bacterium/antimicrobial agent combinations with regard to Gram-positive bacteria, and minor error (intermediate resistant, but susceptible/resistant in the previous method, or susceptible/resistant, but intermediate resistant in the previous method) was 2.2%, major error (false-resistant) was 0.1%, and very major error (false-susceptible) was 0.5%, indicating very high consistency ratio.

Consistency was also observed in 98.6% of 897 bacterium/antimicrobial agent combinations with regard to Gram-negative bacteria, and minor error was 1.4%, major error (false-resistant) and very major error (false-susceptible) were 0%, indicating very high consistency ratio.

These results show much more excellent error rates than the susceptibility testing criteria (CLSI, 2008) of requiring very major error as the most serious error less than 3%, and major and minor errors less than 10% [reference: Clinical and Laboratory Standards Institute (CLSI) (2008) Development of in vitro susceptibility testing criteria and quality control parameters; approved guideline-third edition, M23-A2. Wayne, Pa.: NCCLS)].

According to the present inventive concept, a first culture including a liquid medium treated for subculturing on a solid medium is passed through a pretreatment filter having a mesh structure, thereby effectively removing foreign substances such as cells. Through this process, a process of subculturing the culture on the solid medium, the culture to be used for bacterial identification and antimicrobial susceptibility testing, may be omitted by using the simple filter, and therefore, it is possible to rapidly select appropriate antimicrobial agents for patients, thereby increasing therapeutic efficiency and decreasing the time spent on examination and therapy.

Therefore, the data obtained from the pretreatment method of the present inventive concept were almost consistent with those of the previous method, indicating that there is reliability. The method of the present inventive concept may be used to remarkably reduce the time spent on testing, compared to the previous method, and therefore, the method may greatly contribute to the treatment of bacteremia patients.

Although all elements constituting the embodiments of the present inventive concept are described as integrated into a single one or to be operated as a single one, the present inventive concept is not necessarily limited to such embodiments. In other words, all of the elements may be selectively integrated into one or more and be operated as one or more within the object of the present inventive concept.

Further, it will be understood that the term "including", "constituting", or "having" in the description means that a corresponding element may be included, and other elements may be further included rather than other elements being excluded unless content to the contrary is specially described. Unless defined otherwise, all of terminology used herein, including technical or scientific terms, has the same meanings as those generally understood by one of ordinary skill in the art to which the present inventive concept belongs. Such terms defined in generally used dictionaries are to be interpreted as having meanings equivalent to the contextual meanings in the related art, and not to be interpreted as having ideal or excessively formal meanings unless clearly defined in the specification.

The foregoing is merely illustrative of the technical spirit of the present inventive concept, and various modifications and changes may be made by those skilled in the art to which it pertains without departing from the fundamental characteristics of the inventive concept. Therefore, the exemplary embodiments disclosed herein are for explanation and not for limiting the technical spirit of the present inventive concept, and the scope of the technical spirit of the present inventive concept is not limited by these exemplary embodiments. The scope of protection of the present inventive concept must be interpreted according to the following claims, and it must be interpreted in such a way that all the technical spirits within the equivalent scope of the present inventive concept are included in the scope of the rights of the present inventive concept.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A pretreatment method of a positive blood culture sample for bacterial identification and antimicrobial susceptibility testing, the method comprising:
    preparing a first liquid culture by centrifuging a portion of a liquid medium comprising the positive blood culture sample, washing a precipitate thus centrifuged with a solution including sodium chloride, and suspending the precipitate in the solution including sodium chloride; and
    preparing a second liquid culture by passing the first liquid culture thus prepared through a pretreatment filter comprising a mesh structure.

2. The pretreatment method of the positive blood culture sample for bacterial identification and antimicrobial susceptibility testing of claim 1, further comprising adding a solution comprising ammonium chloride and saponin to the precipitate to lyse blood cells, prior to the washing of the centrifuged precipitate.

3. The pretreatment method of the positive blood culture sample for bacterial identification and antimicrobial susceptibility testing of claim 1, wherein the pretreatment filter is a filter having a conical-configured body comprising an open first end, into which the first liquid medium is introduced, and a second end, from which the second liquid medium obtained by filtering the first liquid medium is discharged, and of which diameter is narrower than that of the first end, and a second end surface is closed with a net having a mesh structure.

4. The pretreatment method of the positive blood culture sample for bacterial identification and antimicrobial susceptibility testing of claim 3, wherein in the pretreatment filter, a portion of the second end surface in the body is composed of the net having a mesh structure, in addition to the second end surface.

5. The pretreatment method of the positive blood culture sample for bacterial identification and antimicrobial susceptibility testing of claim 1, wherein preparing the first liquid culture comprises adding a solution comprising ammonium chloride and saponin to the centrifuged precipitate, followed by vortexing, and then being left at room temperature for a preset time; and
    washing the precipitate being left with a solution comprising sodium chloride, and then suspending the precipitate in the solution comprising sodium chloride to prepare the first liquid culture.

6. The pretreatment method of the positive blood culture sample for bacterial identification and antimicrobial susceptibility testing of claim 1, wherein the second liquid culture obtained by passing through the pretreatment filter is a culture to be used after centrifuging the second liquid culture and suspending a precipitate thus centrifuged in a sodium chloride solution.

\* \* \* \* \*